United States Patent [19]

Muckenfuhs

[11] Patent Number: 5,054,619
[45] Date of Patent: Oct. 8, 1991

[54] SIDE OPENING FLEXIBLE BAG WITH LONGITUDINALLY ORIENTED CARRYING HANDLE SECURED TO SIDE PANELS

[75] Inventor: Delmar R. Muckenfuhs, Middletown, Ohio

[73] Assignee: The Procter & Gamble Company, Cincinnati, Ohio

[21] Appl. No.: 451,498

[22] Filed: Dec. 15, 1989

[51] Int. Cl.⁵ .............................................. B65D 33/06
[52] U.S. Cl. ..................... 206/610; 206/83.5; 206/494; 383/21; 383/25; 383/66
[58] Field of Search ............................ 383/21, 25, 66; 206/610, 494, 83.5

[56] References Cited

U.S. PATENT DOCUMENTS

| | | | |
|---|---|---|---|
| D. 135,538 | 4/1943 | Kaplan. | |
| 655,998 | 8/1900 | Taylor. | |
| 1,261,612 | 4/1918 | Powers. | |
| 1,336,646 | 4/1920 | Mendenhall | 206/610 |
| 1,494,518 | 5/1924 | Whippey | 206/626 |
| 1,733,219 | 10/1929 | Duvall. | |
| 1,920,841 | 8/1933 | Clark | 100/14 |
| 2,011,236 | 8/1935 | Winter et al. | 206/57 |
| 2,127,118 | 8/1938 | Herbelin | 100/14 |
| 2,196,185 | 4/1940 | Belcher | 229/54 |
| 2,270,617 | 1/1942 | Bennett | 229/17 |
| 2,459,130 | 1/1949 | Jones | 229/7 |
| 2,473,492 | 6/1949 | Shina | 229/17 |
| 2,478,412 | 8/1949 | McMahan | 206/47 |
| 2,506,459 | 5/1950 | Holmberg | 93/93 |
| 2,693,304 | 11/1954 | Davis et al. | 226/18 |
| 2,700,459 | 1/1955 | Anspacher | 206/46 |
| 2,750,096 | 6/1956 | Misch | 229/17 |
| 2,766,922 | 10/1956 | Moore | 229/17 |
| 2,781,161 | 2/1957 | Adams | 229/54 |
| 2,866,586 | 12/1958 | Moore | 229/17 |
| 2,998,911 | 9/1961 | Hahn et al. | 229/66 |
| 3,002,674 | 10/1961 | Wright | 229/51 |
| 3,006,119 | 10/1961 | Fingerhut | 53/24 |
| 3,044,228 | 7/1962 | Peterson | 53/24 |
| 3,056,245 | 10/1962 | Baum et al. | 53/24 |
| 3,059,387 | 10/1962 | Fasanella | 53/24 |
| 3,117,513 | 1/1964 | Burnett et al. | 100/215 |
| 3,124,298 | 3/1964 | Repko | 229/66 |
| 3,161,336 | 12/1964 | Loescher | 225/106 |
| 3,173,188 | 3/1965 | Wexler | 28/1 |

(List continued on next page.)

FOREIGN PATENT DOCUMENTS 0258573 3/1988 European Pat. Off. .
0349050 1/1990 European Pat. Off. .

(List continued on next page.)

*Primary Examiner*—Stephen P. Garbe
*Attorney, Agent, or Firm*—E. Kelly Linman; John V. Gorman; Richard C. Witte

[57] ABSTRACT

An easy open flexible bag preferably containing one or more stacks of flexible articles which are maintained in a state of compression in a direction substantially parallel to their thickness. For products such as disposable absorbent baby diapers, catamenial pads, incontinent briefs and the like, the degree of compression within the bag may be as much as 50% or more when compared to the uncompressed thickness of the stack of articles in question. In a particularly preferred embodiment, the bag totally encloses the stack or stacks of compressed flexible articles and exhibits a substantially rectilinear shape. The bag preferably includesa longitudinally oriented carrying handle which is formed indepenently of the bag. The opposed ends of the carrying handle are preferably secured to bag's side panels. The side panels and the front and back panels of the bag are subject to tension imposed by the stack of compressed flexible articles. A predetermined line of weakness spanning a tensioned side wall of the bag is provided and functions as an easy opening system. The easy opening system is so positioned on the side panel of the bag that when the package is opened, the carrying handle remains attached to the bag and fully functional. The easy opening system allows the compressive forces acting upon the flexible articles contained in the bag to be partially relaxed when the easy open feature is activated by the end user. Partial separation or complete removal of a portion of the tensioned side panel of the bag allows the coinciding portion of the stack of compressed articles to project in fan-like array through the aperture thus created to permit easy one-at-a-time removal.

16 Claims, 12 Drawing Sheets

U.S. PATENT DOCUMENTS

| | | | |
|---|---|---|---|
| 3,206,105 | 9/1965 | Smith | 229/55 |
| 3,227,359 | 1/1966 | Hanlon | 229/66 |
| 3,327,449 | 6/1967 | Hullhorst et al. | 53/24 |
| 3,346,166 | 10/1967 | Koolnis | 229/17 |
| 3,354,600 | 11/1967 | Hoffmann | 53/24 |
| 3,361,041 | 1/1968 | Grob | 93/8 |
| 3,370,630 | 2/1968 | Haugh et al. | 150/12 |
| 3,381,440 | 5/1968 | Hullhorst | 53/24 |
| 3,513,628 | 5/1970 | Lee et al. | 53/124 |
| 3,514,033 | 5/1970 | Goodwin | 229/54 |
| 3,548,723 | 12/1970 | Sengewald | 93/35 |
| 3,593,622 | 7/1971 | Sengewald | 93/35 |
| 3,605,570 | 9/1971 | Goodwin | 93/35 |
| 3,626,656 | 12/1971 | Langenscheidt | 53/59 R |
| 3,652,008 | 3/1972 | Grotefend | 206/610 |
| 3,660,964 | 5/1972 | Willis et al. | 53/125 |
| 3,729,886 | 5/1973 | Lucas et al. | 53/24 |
| 3,792,564 | 2/1974 | Brady, Jr. | 53/124 E |
| 3,818,673 | 6/1974 | Rollins et al. | 53/24 |
| 3,824,759 | 7/1974 | Finn et al. | 53/24 |
| 3,908,539 | 9/1975 | O'Brien | 100/49 |
| 3,977,596 | 8/1976 | Gamble | 229/54 |
| 4,031,815 | 6/1977 | Verbeke | 93/33 |
| 4,047,362 | 9/1977 | Lister et al. | 53/189 |
| 4,056,919 | 11/1977 | Hirsch | 53/124 |
| 4,062,169 | 12/1977 | Lister et al. | 53/124 |
| 4,074,508 | 2/1978 | Reid | 53/62 |
| 4,141,193 | 2/1979 | Joa | 53/529 |
| 4,182,237 | 1/1980 | O'Brien | 100/35 |
| 4,216,899 | 8/1980 | Kamp | 229/54 |
| 4,241,562 | 12/1980 | Meyer | 53/438 |
| 4,242,854 | 1/1981 | Nissen | 53/529 |
| 4,252,269 | 2/1981 | Peppiatt | 229/54 |
| 4,328,655 | 5/1982 | Spencer et al. | 53/439 |
| 4,414,788 | 11/1983 | Berg | 53/436 |
| 4,470,511 | 9/1984 | Meeker et al. | 206/610 |
| 4,501,107 | 2/1985 | Piotrowski | 53/438 |
| 4,539,705 | 9/1985 | Baines | 383/8 |
| 4,550,439 | 10/1985 | Peppiatt et al. | 383/8 |
| 4,573,203 | 2/1986 | Peppiatt | 383/8 |
| 4,577,453 | 3/1986 | Hofeler | 53/438 |
| 4,602,472 | 7/1986 | Ampolini et al. | 53/438 |
| 4,604,084 | 8/1986 | Pistner | 493/226 |
| 4,605,392 | 8/1986 | Achelpohl et al. | 493/196 |
| 4,607,388 | 8/1986 | Koiyumaki et al. | 383/121 |
| 4,608,808 | 9/1986 | Ryan et al. | 53/436 |
| 4,609,366 | 9/1986 | Ley et al. | 493/22 |
| 4,610,029 | 9/1986 | Huhtala et al. | 383/10 |
| 4,613,988 | 9/1986 | Maddock | 383/8 |
| 4,628,535 | 12/1986 | Tetenborg | 383/24 |
| 4,632,244 | 12/1986 | Landau | 206/219 |
| 4,633,649 | 1/1987 | Gautier et al. | 53/413 |
| 4,636,191 | 1/1987 | Piggott | 493/227 |
| 4,638,913 | 1/1987 | Howe, Jr. | 206/632 |
| 4,660,352 | 4/1987 | Deines et al. | 53/438 |
| 4,660,354 | 4/1987 | Lancaster et al. | 53/469 |
| 4,661,989 | 4/1987 | Risby | 383/2 |
| 4,664,957 | 5/1987 | van de Pol | 428/35 |
| 4,677,810 | 7/1987 | Spano | 53/428 |
| 4,685,276 | 8/1987 | Kiel | 53/459 |
| 4,686,815 | 8/1987 | Zils et al. | 53/469 |
| 4,688,369 | 8/1987 | Cornish et al. | 53/436 |
| 4,688,370 | 8/1987 | Dighton et al. | 53/469 |
| 4,688,372 | 8/1987 | Langen et al. | 53/529 |
| 4,691,368 | 9/1987 | Roessiger | 383/10 |
| 4,691,369 | 9/1987 | Costa | 383/17 |
| 4,694,638 | 9/1987 | Maddux, Jr. et al. | 53/459 |
| 4,696,050 | 9/1987 | Sengewald | 383/10 |
| 4,696,145 | 9/1987 | Schmidt et al. | 53/436 |
| 4,699,608 | 10/1987 | Pistner | 493/204 |
| 4,702,731 | 10/1987 | Lambrecht et al. | 493/196 |
| 4,703,517 | 10/1987 | Marino | 383/7 |
| 4,704,100 | 11/1987 | Kaufman | 493/194 |
| 4,706,440 | 11/1987 | Bittner | 53/438 |
| 4,710,967 | 12/1987 | Petschner | 383/8 |
| 4,711,066 | 12/1987 | Fox et al. | 53/436 |
| 4,711,067 | 12/1987 | Magni | 53/439 |
| 4,713,135 | 12/1987 | Bridgeford | 156/218 |
| 4,713,839 | 12/1987 | Peppiatt | 383/29 |
| 4,715,635 | 12/1987 | Koskinen | 294/68.1 |
| 4,717,262 | 1/1988 | Roen et al. | 383/120 |
| 4,720,872 | 1/1988 | Kaczerwaski | 383/8 |
| 4,721,396 | 1/1988 | Sengewald | 383/8 |
| 4,730,942 | 3/1988 | Fulcher | 383/7 |
| 4,730,943 | 3/1988 | Johnson | 383/8 |
| 4,738,078 | 4/1988 | Benz et al. | 53/439 |
| 4,738,546 | 4/1988 | Sengewald | 383/7 |
| 4,756,141 | 7/1988 | Hirsch et al. | 53/438 |
| 4,846,587 | 7/1989 | Hull | 383/10 |
| 4,854,733 | 8/1989 | Schwinn | 383/29 |
| 4,874,255 | 10/1989 | Ball et al. | 383/3 |
| 4,934,535 | 6/1990 | Mackenfuhs et al. | 206/610 |

FOREIGN PATENT DOCUMENTS

| | | |
|---|---|---|
| 3102192 | 9/1982 | Fed. Rep. of Germany . |
| 3629563 | 8/1986 | Fed. Rep. of Germany . |
| 3642327 | 8/1986 | Fed. Rep. of Germany . |
| 1022595 | 3/1966 | United Kingdom . |
| 1282769 | 7/1972 | United Kingdom . |
| 2035258 | 6/1980 | United Kingdom . |

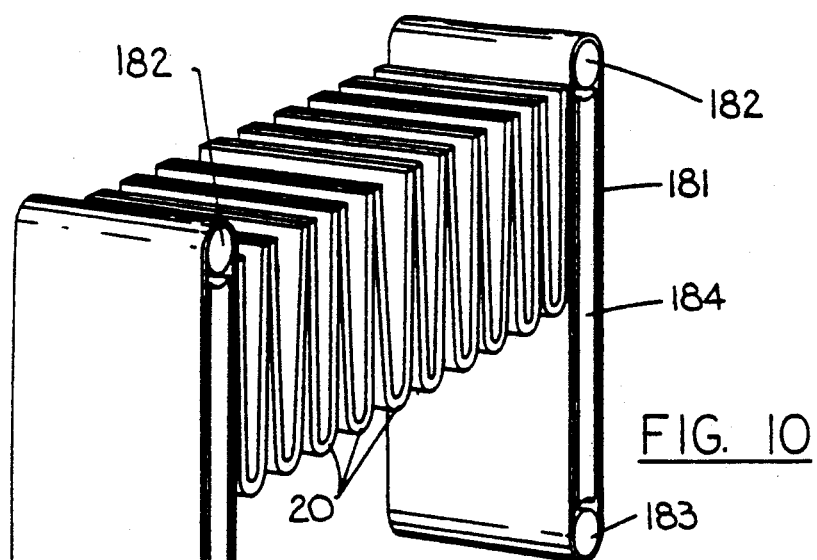
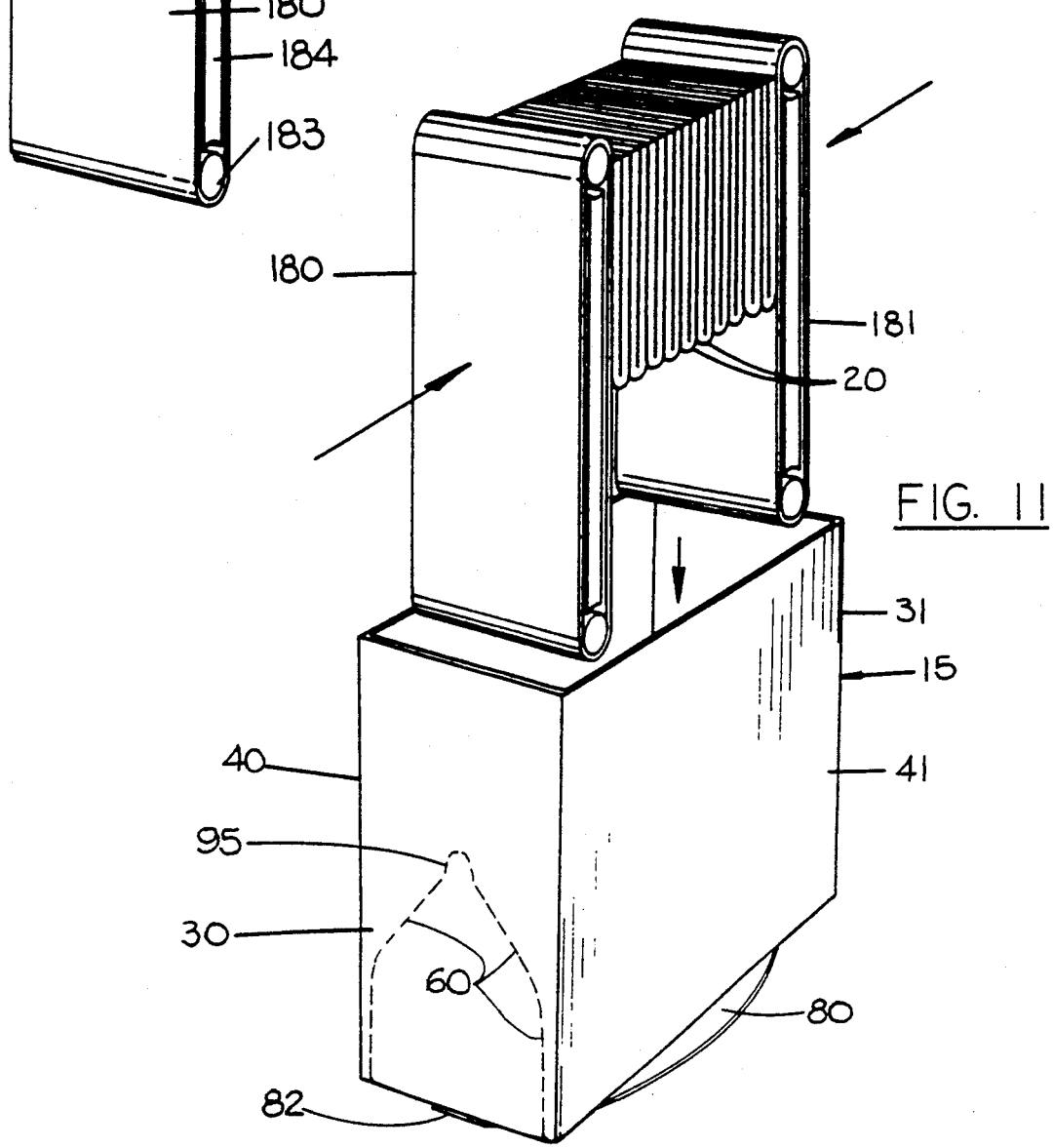

SIDE OPENING FLEXIBLE BAG WITH LONGITUDINALLY ORIENTED CARRYING HANDLE SECURED TO SIDE PANELS

TECHNICAL FIELD

The present invention relates to an easy open flexible bag having a longitudinally oriented carrying handle, said bag being filled with a multiplicity of articles which are normally used one at a time.

The present invention further relates, in a particularly preferred embodiment, to such an easy open bag wherein the articles contained therein are comprised of compressible material, such as disposable absorbent bandages, baby diapers, sanitary napkins, incontinent briefs and the like.

The present invention further relates to such an easy open bag wherein the articles in question are compressed in a direction perpendicular to their thickness and wherein said bag maintains said articles in a state of compression until activation of the easy open feature.

The present invention further relates to such an easy open flexible bag which, upon activation of the easy open feature, will permit the compressed articles to partially expand from the inner confines of the bag to produce a fan like array of articles to permit easy one-at-a-time removal of the articles from the bag.

The present invention further relates to such an easy open flexible bag wherein the compressed articles tend to automatically feed into the aperture formed in the bag by activation of the easy open feature, at least until such time as the articles remaining within the bag return to their initially uncompressed thickness.

The present invention further relates to such an easy open flexible bag which, upon opening, allows easy access to the product therein without reducing the functionality of the longitudinally oriented carrying handle.

The present invention further relates to such an easy open flexible bag which can be constructed of relatively low cost flexible materials such as polymeric films, papers, nonwovens, or laminate structures comprised of two or more such low cost materials.

BACKGROUND ART

Relatively soft and flexible compressible articles such as disposable diapers, catamenial pads, incontinent briefs and the like have entered widespread use in many parts of the world over the last 20-30 years. Many of these products are produced as continuous webs which are typically folded one or more times parallel to the direction of web travel as they travel through the converting lines in the machine direction and are ultimately cut from the web to form discrete single use articles. The discrete articles are typically folded at their midpoint, collected in stacks and inserted into paperboard or cardboard cartons or flexible bags while they are subject to little or no compression in a direction substantially parallel to their thickness.

In such circumstance, the dimensions of the paperboard or cardboard carton or flexible bag are generally determined by the number of discrete articles contained in the stack or stacks placed within the carton or bag.

Recent consumer purchasing trends in the disposable absorbent products field, particularly in the United States, have led to lower purchase frequencies with larger quantities of disposable absorbent products per purchase. Manufacturers have responded by continuing to increase the number of discrete articles contained within a single package, resulting in a number of jumbo packs containing relatively large quantities of disposable absorbent products such as baby diapers, e.g., 32, 44, 48, 64, 96, etc. Because of the bulk of the relatively low density flexible compressible articles in question, this has resulted in packages having high volume but low weight. This combination of high volume and low weight increases storage and handling costs for the manufacturer, rapidly exhausts the limited shelf space of the retailer, and detracts from the convenience of storage and use for the consumer.

In addition, the relatively large volume of package material required to house the disposable absorbent articles in an uncompressed condition must be disposed of when the package in question has been fully emptied. In the case of cartons, this requires further effort by the end user to crush or otherwise minimize the volume of the empty container before placing it in the trash.

OBJECTS OF THE INVENTION

Accordingly, it is an object of the present invention to overcome or at least reduce the severity of the aforementioned storage, handling and disposability problems associated with prior art packages of substantially uncompressed flexible articles, while simultaneously providing improved convenience for and acceptance by the end user.

It is another object of the present invention to provide an easy open flexible package of compressed flexible articles which can simultaneously overcome many of the problems of the prior art packages of substantially uncompressed articles, as described in the preceding paragraphs, while simultaneously reducing the costs incurred by the manufacturer.

It is another object of the present invention to provide an easy open flexible bag having a carrying handle and filled with one or more stacks of compressed flexible articles. Such a bag can be comprised of relatively inexpensive materials such as polymeric films, papers, nonwovens, or a laminate comprising two or more of such materials, thereby decreasing the severity of the disposal problem from an environmental standpoint both with respect to the amount of packaging material required and the disposability/degradability of the particular bag material selected.

It is another object of the present invention to provide an easy open flexible bag of compressed flexible articles which exhibits an unobstructed opening feature which can readily be found by the end user and which can be easily and reliably opened by gripping with the user's fingers and tearing along a predetermined line of weakness in the bag material, all without impairing the functionality of the longitudinally oriented carrying handle.

It is another object of the present invention to provide such an easy open flexible bag filled with compressed flexible articles which, upon activation of the easy open feature, will cause the unrestrained portion of the compressed articles housed within the bag to partially project in a fan-like arrangement through the aperture created in the tensioned side panel of the bag. This permits easy one-at-a-time removal of discrete articles from the bag, at least until such time as the compressive forces acting upon the articles remaining in the bag have been substantially relieved.

It is still another object of the present invention to provide an easy open flexible bag which will offer improved convenience in carrying and opening and improved access to the bag's contents even when employed in situations where the articles contained within the bag are not subject to any appreciable compression, said easy open feature being so constructed that it will not impair the functionality of the longitudinally oriented carrying handle even after the bag has been opened.

DISCLOSURE OF THE INVENTION

The present invention, in a particularly preferred embodiment, comprises an easy open top gusseted flexible bag having a longitudinally oriented carrying handle secured to the bag's side panels, said bag containing one or more stacks of flexible articles maintained in a state of compression in a direction substantially parallel to their thickness. As described herein, a top gusseted bag is one wherein the gussets which are ultimately aligned parallel to the side panels of the bag are comprised of material which was originally an extension of the top panel. The direction of compression of said flexible articles is also preferably parallel to the length of said longitudinally extending carrying handle. In a particularly preferred embodiment, the ends of the longitudinally extending carrying handle are secured to the inwardly folded top gusset portion of the opposing side panels. For products such as disposable absorbent baby diapers, catamenial pads, incontinent briefs sand the like, the degree of compression within the bag may be as much as 50% or more when compared to the uncompressed thickness of the stack of articles in question.

In a particularly preferred embodiment, the top gusseted bag totally encloses the stack or stacks of compressed articles and exhibits a substantially rectilinear shape. The flexible bag preferably comprises a front and back panel connected to one another at the sides by a seal to form a pair of opposing side panels. The preferred package has a longitudinally oriented carrying handle located on the top of the package. The handle is preferably formed independently of the bag and its opposed ends are secured to the top portion of the opposing side panels of the bag, most preferably to the inwardly folded top gusset portion of each side panel. At least one stack of compressed articles oriented so that their substantially planar surfaces are aligned substantially parallel to the side panels of the bag is preferably totally enclosed within the bag by forming inwardly folded side gussets from the lowermost ends of the opposing side panels and thereafter connecting the lowermost ends of the front and back panels of the bag to one another to form a bottom panel The side panels and the front and back panels are preferably subject to tension imposed by the stack of compressed flexible articles.

The sealed bag also includes an easily visible, unobstructed easy open device which may be activated by gripping between the user's fingers and pulling to create a substantially unobstructed aperture in one side of the bag.

The easy opening device employed in a particularly preferred embodiment of the present invention comprises a predetermined line of weakness on one of the side panels of the bag. The line of weakness can be formed by many means well known in the art, including, for example only, perforations in the bag material. The portion of the line of weakness contained within the side panel in question exhibits a shape approximating up to about 75%, and hence up to about 75% of the total surface area of one of the substantially planar surfaces of one of the articles contained in the cross-sectional shape of the stack of compressed articles housed within the bag. In the case where stacks of articles are superposed on one another, an ancillary line or lines of weakness are preferably provided in order to permit further extending the aperture down the side panel as the initial stack of articles is exhausted.

BRIEF DESCRIPTION OF THE DRAWINGS

While the specification concludes with claims particularly pointing out and distinctly claiming the present invention, it is believed the present invention will be better understood from the foregoing description in conjunction with the accompanying drawings in which:

FIG. 10 is a simplified schematic illustration of a pair of knife belt assemblies which are preferably employed to compress a stack of flexible articles to be housed within an easy open flexible bag of the present invention, said view being taken prior to compression of the stack of flexible articles;

FIG. 11 is a simplified perspective view of the apparatus of FIG. 10 shown after the stack of flexible articles has been compressed, but prior to inserting of the knife belt assemblies and the stack of compressed articles into the bottom of a partially pre-erected easy open flexible bag of the present invention;

DETAILED DESCRIPTION OF THE INVENTION

While the present invention will be described in the context of providing an easy open flexible bag containing one or more stacks of folded disposable absorbent diapers, the present invention is in no way limited to such application. Furthermore, while the illustrated embodiments of the invention disclose folded disposable diapers which are maintained in a state of compression in a direction substantially parallel to their thickness, many of the benefits of the easy open feature of the present invention may also be provided in packages wherein the objects contained therein are not subject to compressive forces. Thus, it is not a requirement of the present invention that the articles contained within the flexible bag be held in a state of compression by the bag prior to opening.

As pointed out earlier herein, the present invention may be practiced to greatest advantage to provide reduced storage, shipping and handling costs in any situation involving flexible articles which are substantially compressible in at least one of their dimensions, such as their thickness. In addition, the present invention can be practiced to great advantage to provide automatically assisted dispensing of discrete flexible articles one at a time due to the action of the compressive forces acting upon the flexible articles during a substantial portion of the bag's usable life. The detailed description contained herein, which relates to a particularly preferred easy open flexible bag of compressed disposable diapers, will allow one skilled in the art to readily adapt the invention to other uses.

Figure 1:
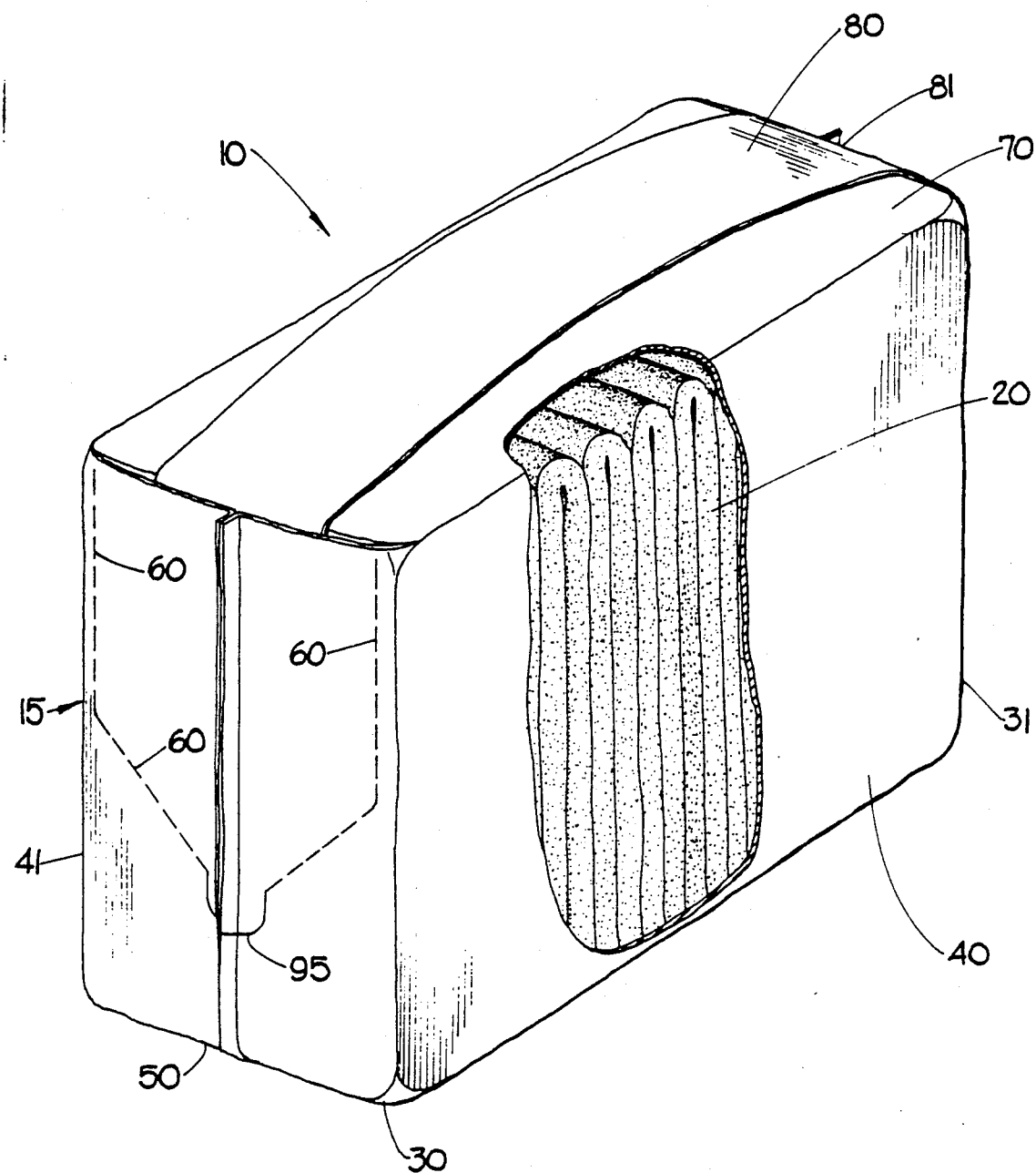
FIG. 1 is a simplified perspective view of a particularly preferred easy open flexible bag of compressed flexible articles of the present invention.

FIG. 1 is a simplified perspective illustration of a particularly preferred embodiment 10 of an easy open flexible bag of compressed flexible articles 20 of the present invention. The compressed flexible articles 20 may comprise disposable absorbent diapers such as those disclosed in commonly assigned U.S. Pat. No. 3,860,003 issued to Buell on Jan. 14, 1975 and hereby incorporated herein by reference. Prior to stacking and insertion into the bag, the diapers 20 are typically folded one or more times in a direction generally parallel to the machine direction during converting so that the ears of each hourglass shaped diaper overlie the central portion of the diaper. The diapers 20 are also preferably folded about their midpoints after being cut from a continuous web and prior to being collected into stacks. The resultant cross-section of each stack of diapers 20 is substantially rectangular. In the embodiment shown in FIG. 1, one such stack is provided so that the side panels 30 and 31 of the flexible bag 15 are substantially equal to the cross-section of one stack of diapers 20.

Prior to insertion into the bag 15, the stacks of folded disposable diapers 20 are subjected to compression to reduce the overall dimension of the stack by as much as 50% or more relative to the uncompressed height of the stack.

As can be seen from FIG. 1, the stacks of compressed diapers 20 are maintained in their compressed state by opposing side panels 30 and 31 which are joined at their lateral edges to front panel 40 and back panel 41. Accordingly, these panels remain in tension at least until the compressive forces acting upon the diapers remaining in the bag have been relieved.

Flexible bag 15 illustrated in FIG. 1 is preferably formed by folding a web of film, paper or other suitable material such that a top gusset 90,91 is formed at each of the opposing free edges of the top panel 70 of the bag. The opposing ends of an auxiliary member comprised of film, paper or other suitable material which will function as a carrying handle 80 are preferably secured at areas 81 and 82 to the opposed top gussets 90,91, respectively, and the top gussets 90,91 are thereafter folded parallel to the sides of the bag.

Various techniques for securing a handle or carrying strap to the side panels of a gusseted bag are known. See, for example, British Patent No. 1,022,595 filed in 1963; U.S. Pat. No. 3,370,630 issued to Haugh et al.; U.S. Pat. No. 4,539,705; U.S. Pat. No 4,550,439 issued to Peppiatt et al. on Oct. 29, 1985; and U.S. Pat. No. 4,730,943 issued to Johnson on Mar. 15, 1988, all of said patents being hereby incorporated herein by reference. The particular method of securing the ends of the handle or carrying strap to the side panels of a flexible bag of the present invention is non-critical.

FIGS. 6 through 9 are a simplified schematic of one construction sequence which may be employed to secure a carrying strap 80 to the side panels 30,31 of a gusseted bag of the present invention.

Figure 6:
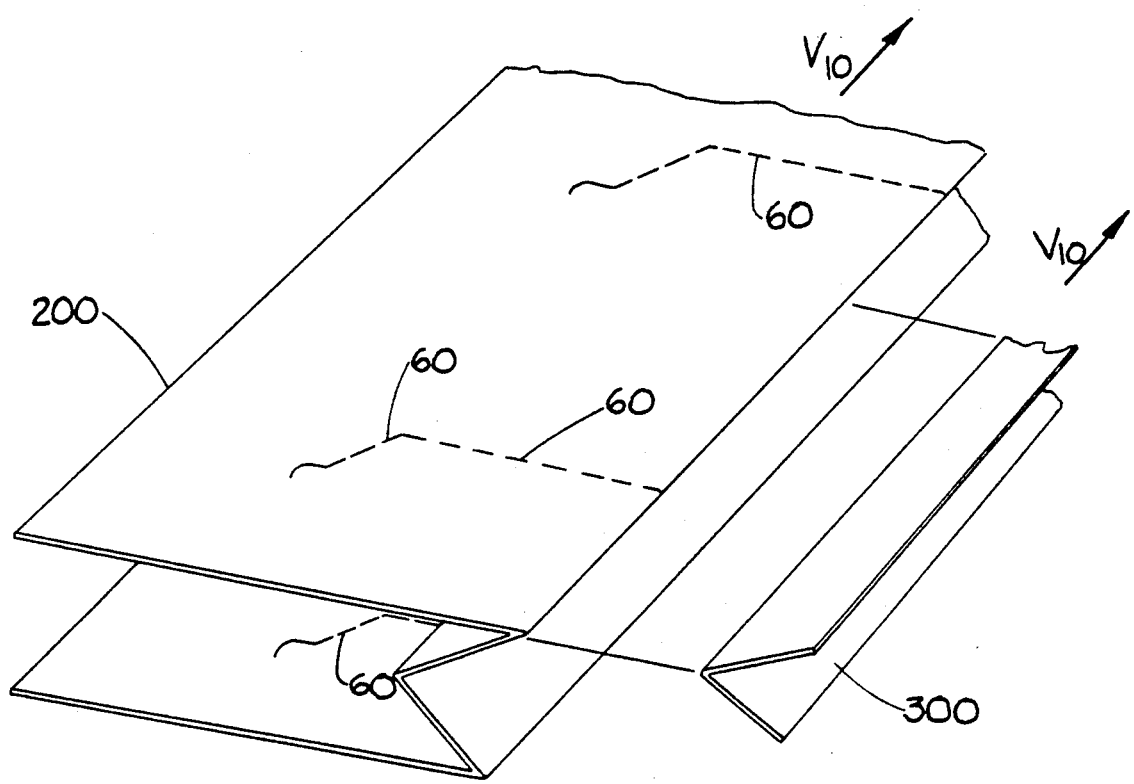
FIG. 6 is a simplified schematic illustration of how flexible handled bags of the present invention may be formed from moving, folded webs.
Figure 7:
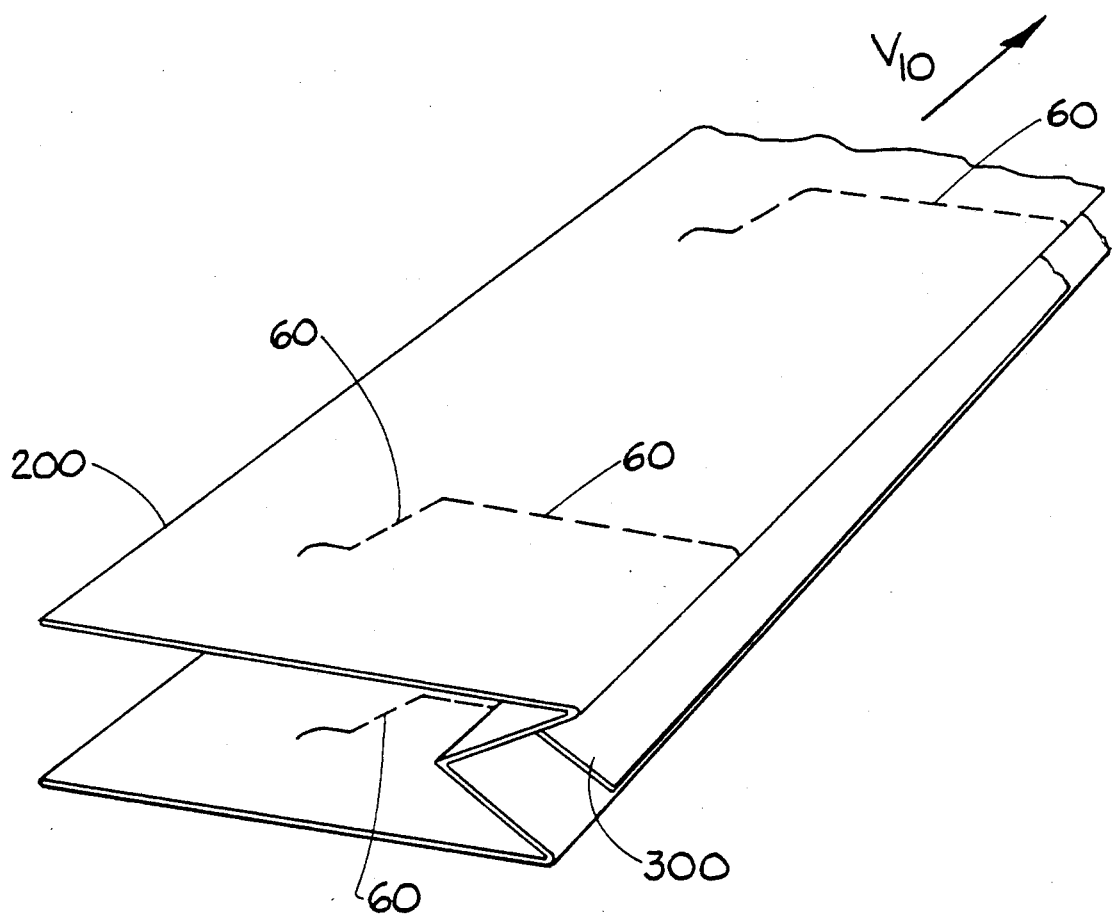
FIG. 7 is a view of the moving folded webs of FIG. 6 after the webs have been nested with one another.

In FIG. 6 there is shown a schematic illustration of a folded web of bag material 200 moving in the machine direction at a velocity $V_{10}$. The cross-section of the moving web of material 200 is in the basic shape of a "W" with the outermost legs of the "W" in a substantially horizontal orientation. Prior to folding, the web 200 is provided with at least two discrete portions of a line of weakness 60 at predetermined spaced locations along its length. The two discrete portions of each line of weakness 60 are so positioned in web 200 that when the web is folded into a "W", the two portions of each line of weakness 60 which are located only in the outermost leg portions of the "W" substantially coincide with one another, as generally shown in FIGS. 6 and 7. A second web of material 300 which is used to form the carrying handle is folded in the shape of a "V" is also travelling in the machine direction at a velocity $V_{10}$, identical to that of the moving web of bag material 200. The legs of the V-shaped web of material 300 are preferably sized so that they will fit within the V-shaped portion of the "W" in the moving web of bag material 200.

FIG. 7 illustrates the condition which exists after the V-shaped web of handle material 300 has been inserted within the V-shaped portion of the "W" comprising the moving web of bag material 200.

Figure 8:
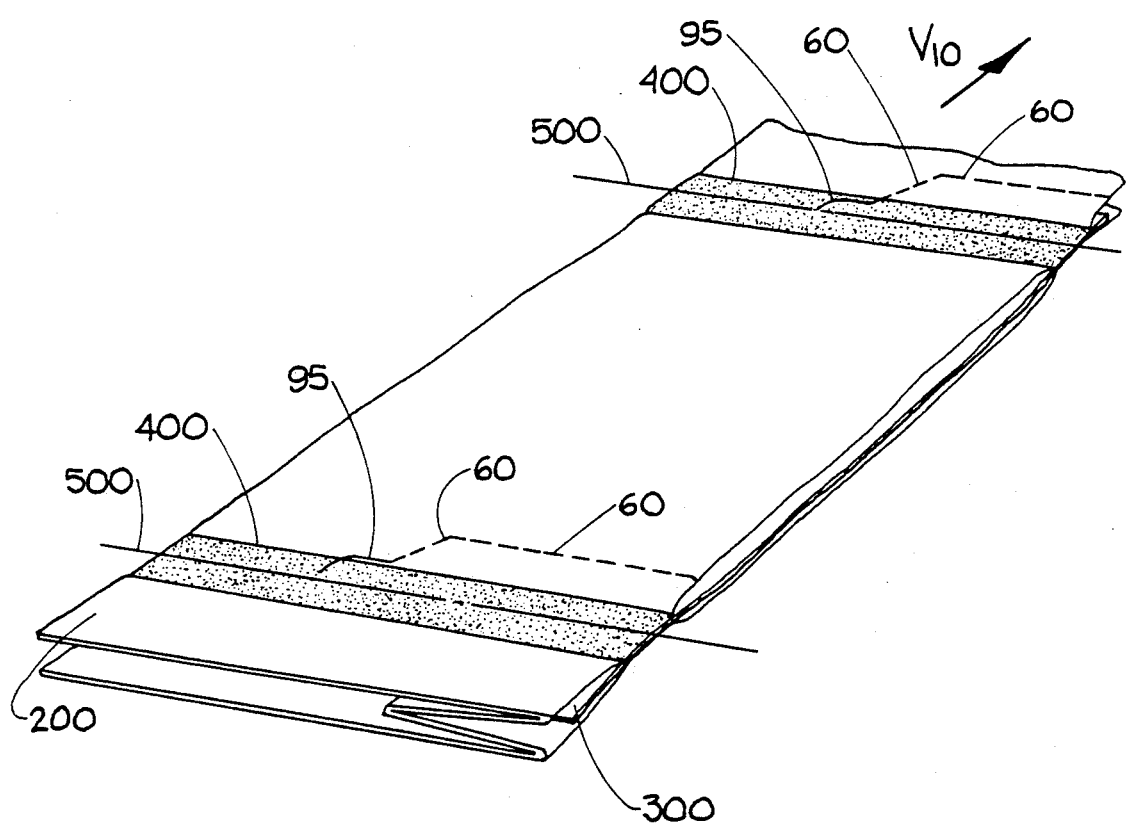
FIG. 8 shows the nested webs of FIG. 7 after they have been sealed to one another at predetermined locations along their length.

FIG. 8 illustrates the condition of the web after the nested webs 200 and 300 have been secured together, as by heat sealing, adhesives, etc., at predetermined spaced locations along their length to form sealed areas 400 extending across the entire width of the nested webs. At this point, the nested, sealed webs are still moving in the machine direction at velocity $V_{10}$.

Figure 9:
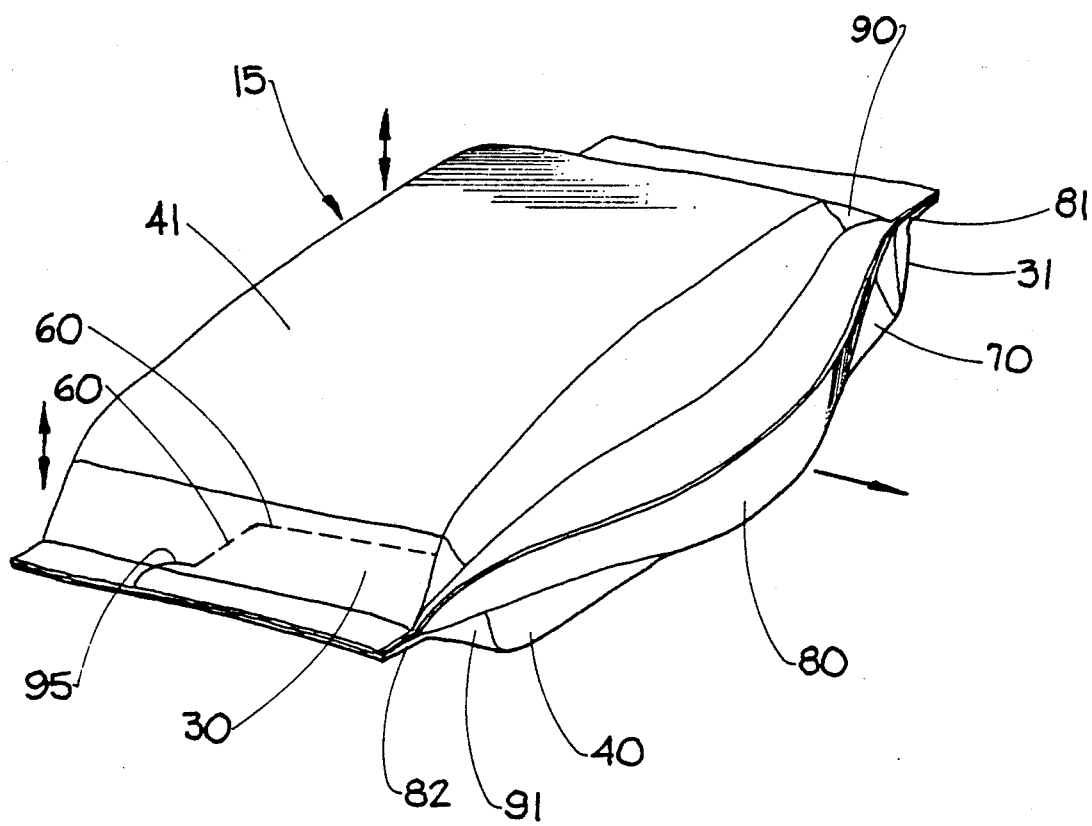
FIG. 9 shows a bag cut from the continuous web of FIG. 8 as the bag is being partially erected to form an extended carrying handle and an open bottom ready for loading.

FIG. 9 illustrates the condition which exists after individual bags have been cut from the moving web along center lines 500 shown in FIG. 8. Each heat seal area 400 in the moving web thus functions to provide the trailing side seal of one bag and the leading side seal of the adjacent bag.

As can also be seen in FIGS. 8 and 9, the sealed areas 400 coincide with the discrete portions of each line of weakness, such that when the flexible bags 15 cut from the web are erected, a substantially continuous line of weakness 60, the lowermost portion of which converges to form an arrow having a tip pointing generally in the direction of the bottom of the bag, will span each side panel 30. The tip of the arrow includes a readily accessible grasping tab 95 comprising a tear initiating point for initiating tears along line of weakness 60.

FIG. 9 shows a discrete bag 15 generally similar to that shown in FIG. 1 as the bag is being erected from a substantially collapsed condition to a substantially erected condition for insertion of the compressed flexible products into the open bottom end of the bag. The full extent of continuous line of weakness 60, which appears only partially in FIGS. 8 and 9, is shown in FIG. 11, which shows flexible bag 15 with its side panel 30 fully erected.

FIG. 9 also illustrates the manner in which top gussets 90 and 91 are folded so as to be aligned substantially parallel to side walls 31,30, respectively.

As will be appreciated by those skilled in the art, the particular manner of forming the flexible bag and attaching the end portions of the carrying handle 80 thereto is noncritical to the practice of the present invention.

At least one stack of compressed articles 20 oriented so that their substantially planar surfaces are aligned substantially parallel to the side panels 30,31 of the bag is preferably totally enclosed within the bag by forming inwardly folded gussets from the lowermost ends of the opposing side panels and thereafter connecting the lowermost ends of the front and back panels 40,41 of the bag to one another to form a bottom panel 50. The manner of inserting the compressed articles 20 into the flexible bag 15 through its open bottom can, if desired, be in accordance with the method schematically shown in Drawing FIGS. 10-15.

FIGS. 10-15 schematically disclose a particularly preferred method and apparatus for compressing a stack of flexible articles 20 to be housed within an easy open flexible bag 15 of the present invention and for reliably inserting the stack of compressed articles through the open bottom of a partially pre-erected flexible bag of the present invention.

In particular, FIG. 10 illustrates a stack of disposable diapers 20 prior to compression between a pair of opposing knife belt assemblies. Each knife belt 180,181 rotates about an uppermost roller 182 and a lowermost roller 183. Either the uppermost or lowermost roller must be provided with suitable drive means capable of moving the knife belts 180,181 in the direction shown by the arrows. A smooth surfaced belt support member 184 is preferably located intermediate each pair of rollers 182,183. The opposing ends of each belt support member 184 exhibit an inwardly concave shape approximating that of the adjacent roller to maximize the area of contact between the belt support member 184 and its respective knife belt. Each belt support member 184 is preferably secured in fixed relation to the axis of rotation of the adjacent uppermost roller 182 and the adjacent lowermost roller 183. Each knife belt assembly is laterally moveable in a direction which will compress the stack of flexible disposable diapers 20 located between the knife belts 180,181, as generally shown in FIG. 11. Each knife belt assembly is also vertically moveable so that the knife belts 180,181 containing the stack of compressed disposable diapers 20 can be inserted within the open bottom end of the partially pre-erected flexible bag 15, also as generally shown in FIG. 11.

Alternatively, knife belts 180,181 may be vertically fixed and the partially pre-erected bags 15 may be moved onto and off of the vertically stationary knife belts by suitable bag moving apparatus (not shown). In still another embodiment (not shown) the knife belts and the bags may both move relative to one another.

Figure 12:
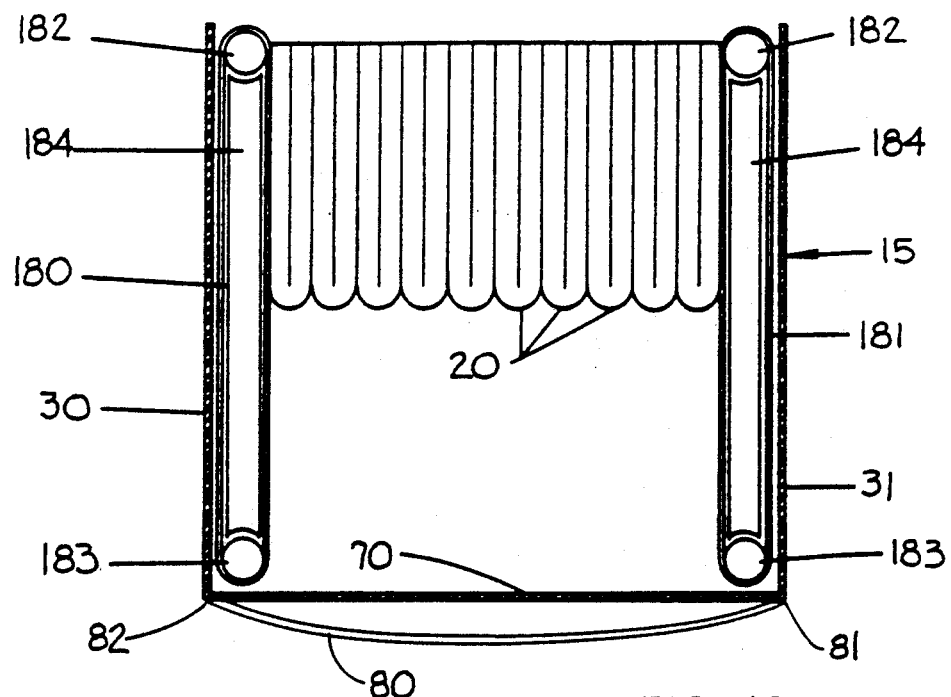
FIG. 12 is a simplified cross-sectional view of the knife belt assemblies and the bag of FIG. 11 after the knife belt assemblies have been inserted within the confines of the partially pre-erected bag.

FIG. 12 illustrates the condition which exists when the knife belt assemblies including knife belts 180,181 have been inserted within the open bottom end of the partially pre-erected flexible bag 15. The amount of compression applied to the flexible disposable diapers 20 is sufficient to allow the compressed stack of disposable diapers and the knife belts 180,181 to pass within the open bottom end of the flexible bag 15 without interference.

Figure 13:
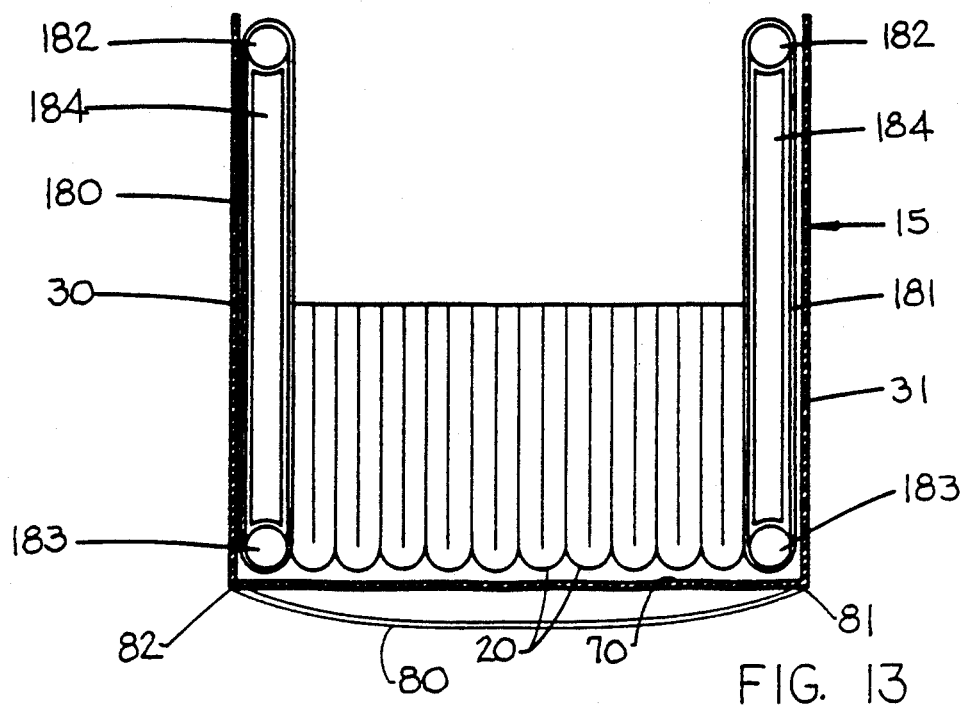
FIG. 13 is a cross-sectional view generally similar to that of FIG. 12, but showing the position of the stack of compressed articles after the knife belts have driven them into contact with the innermost surface of the top panel of the partially pre-erected bag.

Once inside the partially pre-erected flexible bag 15, the drive means for knife belts 180,181 are activated to advance the compressed disposable diapers 20 into final position against the innermost surface of top panel 70 of the partially erected flexible bag 15, as generally shown in FIG. 13. Because the knife belts 180,181 do not contact the innermost surfaces of end panels 30,31 of the flexible bag, no distortion of the flexible bag is caused by activation of the belts.

To withdraw the knife belt assemblies from the open bottom end of the flexible bag 15, the knife belt assemblies are simultaneously extracted without changing their lateral spacing from one another at a first velocity $V_1$. To prevent removal of the compressed disposable diapers 20 from the open bottom end of the bag, the belts 180,181 are driven in the direction shown by the arrows in FIG. 14 at a second velocity $V_2$, which is equal to or slightly greater to the velocity of retraction VI of the knife belt assemblies. This maintains the compressed disposable diapers 20 in intimate contact with the innermost surface of top panel 70 of the flexible bag 15.

In the event the knife belts 180,181 are maintained vertically stationary and the flexible bags are inserted onto and off of the knife belts, then the belts should be operated at a velocity which is equal to or slightly greater than the velocity of bag retraction to maintain the compressed disposable diapers seated within the bag. A corresponding velocity relationship between the speed of the knife belts 180,181 and the speed of bag retraction should be established for the embodiment wherein both the knife belts and the bags move relative to one another is employed.

Figure 14:
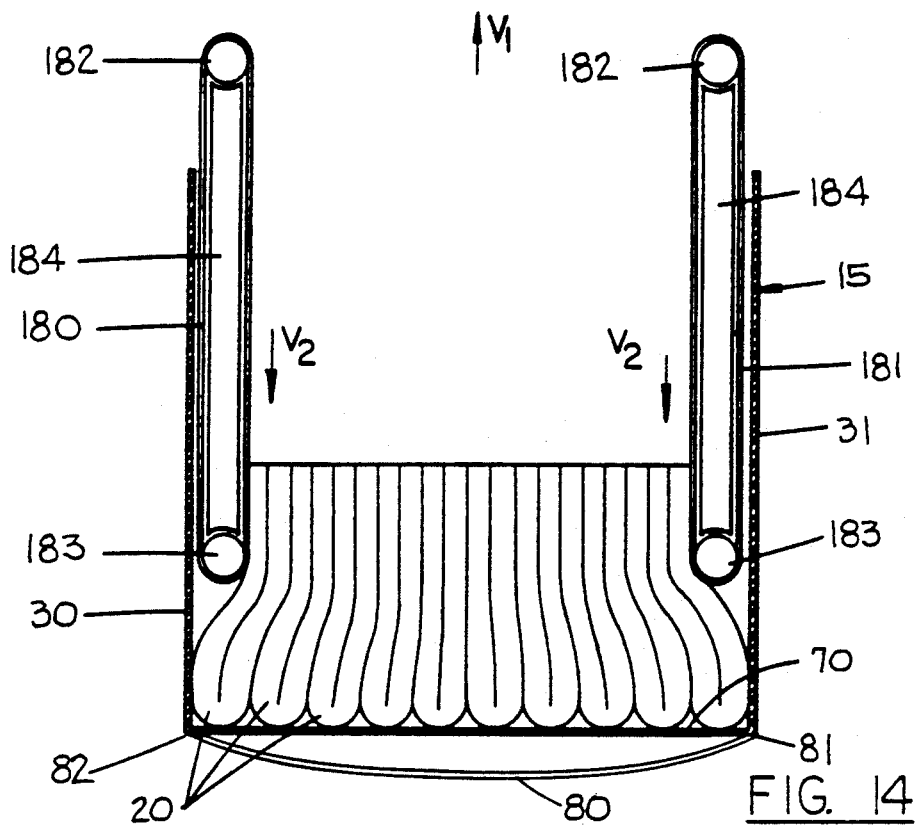
FIG. 14 is a cross-sectional view of the system shown in FIG. 13 as the knife belt assemblies are being retracted from the confines of the bag at a first velocity $V_1$, while the knife belts are operating at a second velocity $V_2$, which is equal to or slightly greater than the velocity of retraction $V_1$.
Figure 15:
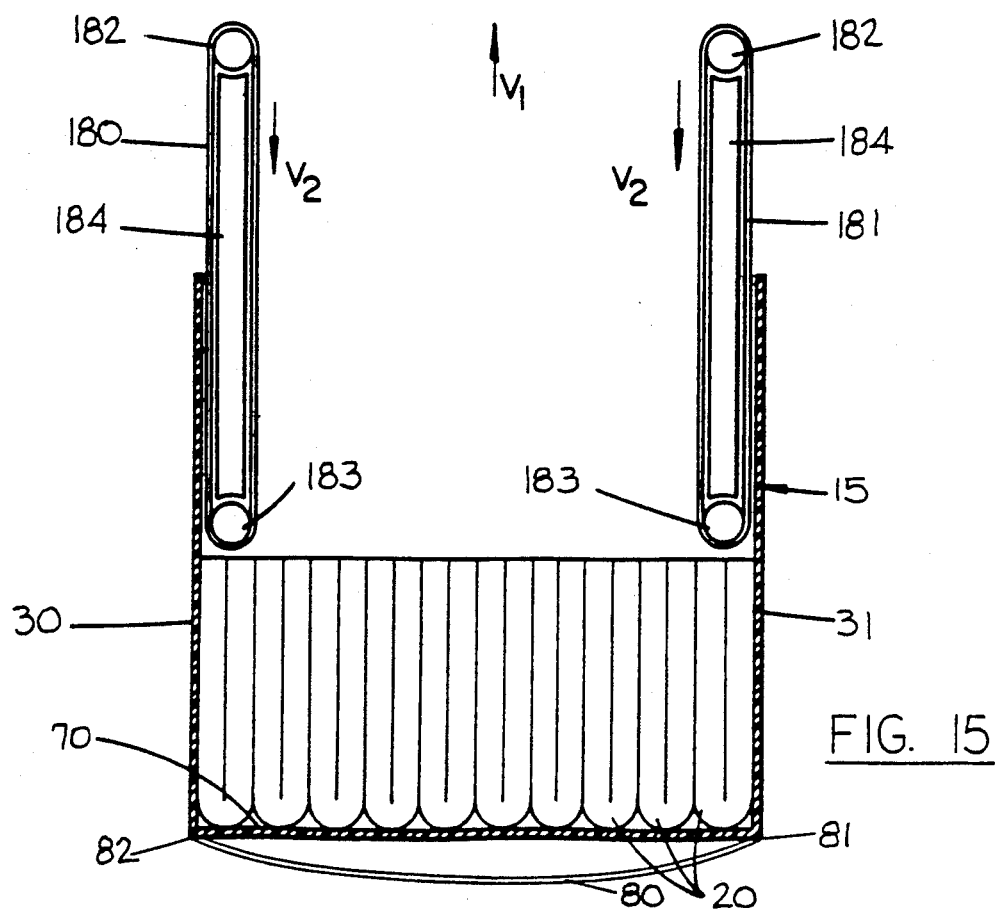
FIG. 15 shows the condition which exists after the knife belts shown in FIG. 14 have completely released control of the stack of compressed flexible articles.

As can also be observed from FIG. 14, the compressed disposable diapers 20 begin to expand immediately as the knife belts 180,181 release control of the stack. This results in the condition generally illustrated in FIG. 15, i.e., the compressed disposable diapers 20 have expanded to occupy the full interior cross-section of the flexible bag 15, thereby relieving, at least to a degree, some of the compression initially imparted to the stack of articles 20 by the knife belts 180,181. As will be appreciated by those skilled in the art, if the amount of compression remaining in the stack of flexible articles within the flexible bag 15 is to be about 50%, then the initial compression which must be imparted by the knife belts 180,181 must be greater than 50%, e.g., perhaps as much as 60% or 70%.

Once the knife belt assemblies have been fully removed from the open bottom end of the flexible bag 15, the open bottom end of the bag is preferably folded in gusset style and the opposing portions of the front and back panels are sealed to one another to form a substantially untensioned bottom panel 50, as generally shown in FIG. 1.

In the illustrated embodiment of FIG. 1, the tension required to keep the disposable absorbent diapers 20 in a compressed state is carried by side panels 30 and 31 and front and back panels 40 and 41. Bottom panel 50 and top panel 70 are in a substantially untensioned condition.

The easy open feature of flexible bag 15 comprises a substantially continuous line of weakness which traverses side panel 30 in an area generally coinciding with the stack of disposable diapers 20. In the embodiment illustrated in FIG. 1, the substantially continuous line of weakness comprises line of perforations 60 in side panel 30. A readily visible and graspable gripping tab 95 is preferably provided along the lowermost portion of the line of perforations 60.

Figure 2:
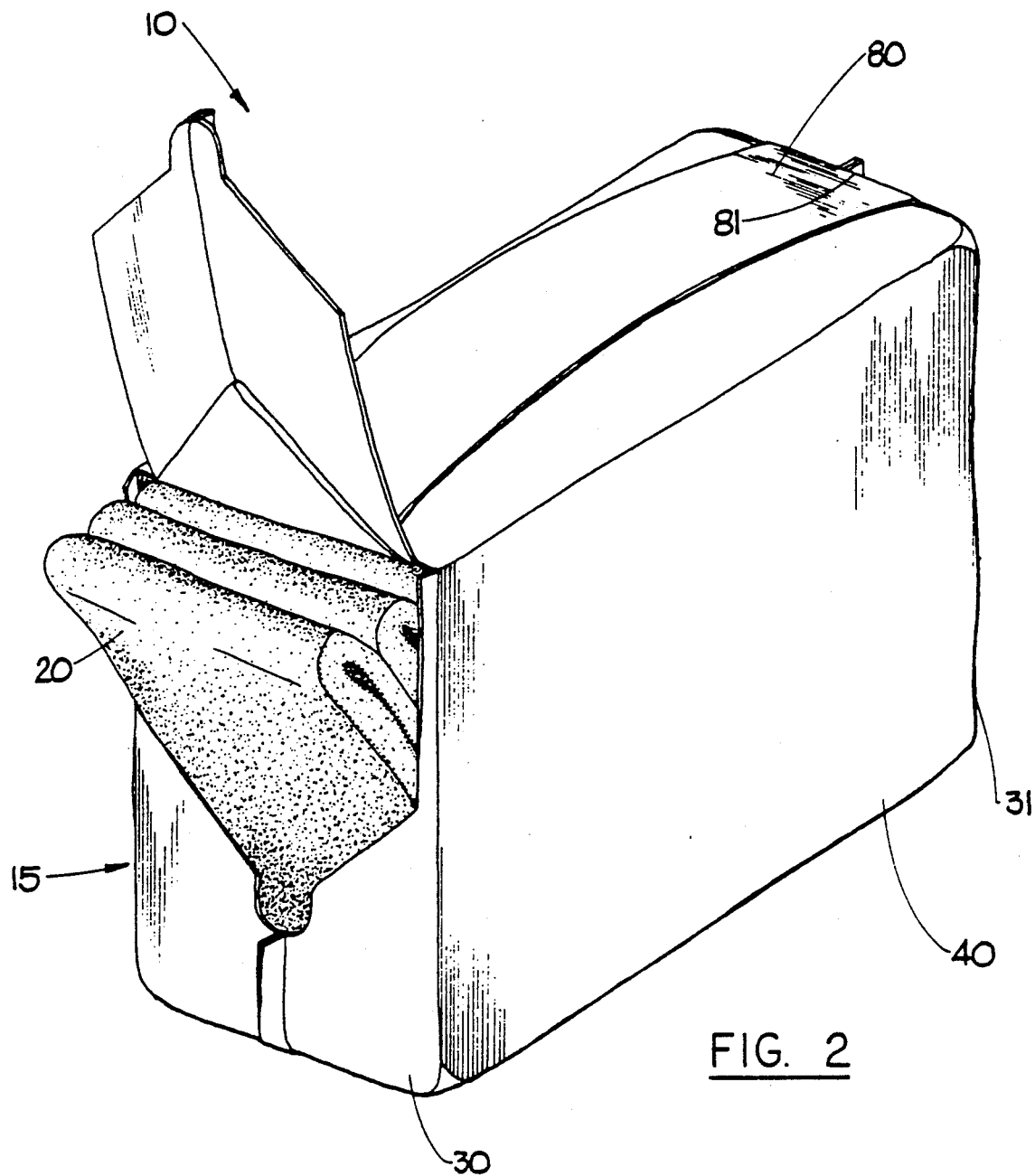
FIG. 2 is a similar simplified perspective view of the bag of FIG. 1, but showing the conditions which exist after the side opening segment has been partially removed and the unrestrained portion of the diapers are bulging out of the opened package.

As can best be seen from FIG. 2, the unrestrained folded edges of the compressed disposable diapers 20 begin to project through the aperture spanning the tensioned side panel 30 in a fan-like array when the easy open feature is activated. This is due to a partial release of the compressive forces acting upon the stack of compressed disposable diapers 20 contained within the flexible bag 15. Note from FIG. 2, however, that the uppermost end of the material which is partially separated from side wall 30 remains attached to flexible bag 15. Accordingly, the end of carrying handle 80 secured to side panel 30 at area 82 remains completely functional if the user desires to carry the bag by its handle after opening.

As will be appreciated by those skilled in the art, it is necessary to retain at least a portion of the cross-sectional shape of the stack of folded compressed diapers 20 subject to compression in order to produce the automatic fan-like array illustrated in FIG. 2. While FIG. 2 depicts removal of about 60% of the height of the uppermost stack of diapers, leaving about 40% of the depth of the stack of diapers subject to compressive restraint, it has been determined that easy open flexible bags of the present invention can employ apertures spanning up to about 75% of the vertical depth of the compressed stack of products while still maintaining control of the lowermost portion of the stack.

In general, it has been observed that it is preferable to provide the portion of line of weakness 60 contained within the tensioned side panel 30 with a shape which converges slightly from the top corners of the bag to assist in providing better overall retention of the stack of compressed articles 20 within the bag without impeding the ability of the uppermost portion of the articles 20 to automatically project in fan-like array through the uppermost portion of the aperture formed in the tensioned side panel 30. This restraining action might be likened to the use of a pair of suspenders to hold up the waistband of a pair of trousers on a person having a rotund midsection, i.e., the rotund midsection projects forwardly between the suspenders.

Figure 3:
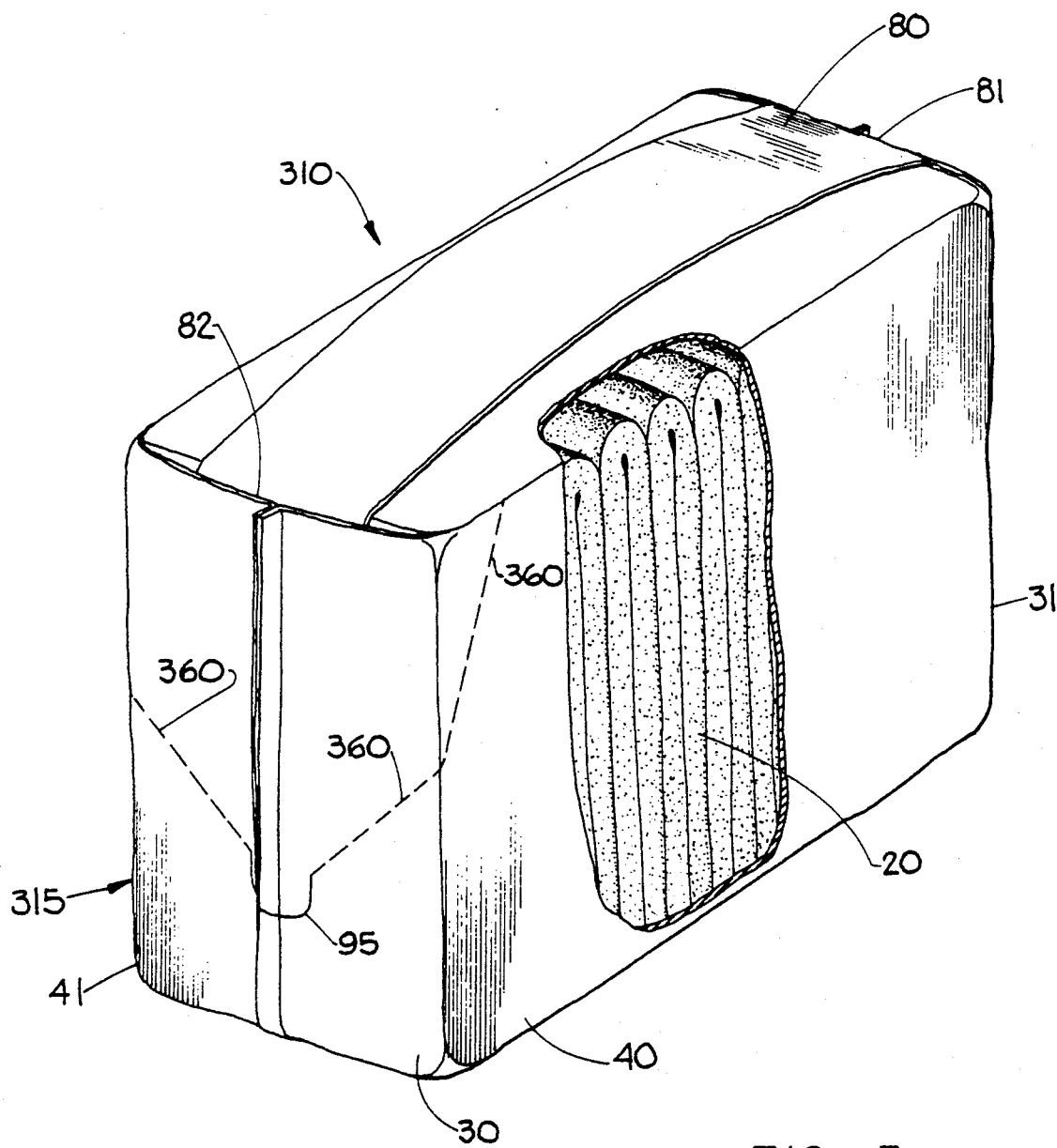
FIG. 3 is a view of an alternative flexible bag of compressed flexible articles of the present invention illustrating an opening device for partially removing a greater portion of the bag, the predetermined line of weakness extending to a degree into the front and back panels of the bag, said view being taken before activation of the easy opening feature.

FIG. 3 discloses an alternative flexible package 310 of compressed disposable diapers 20 which is in most regards generally similar to embodiment 10 shown in FIG. 1. However, the continuous line of weakness is comprised of a continuous line of perforations 360 spanning not only side panel 30, but also the uppermost edges of front and back panels 40 and 41, respectively. Flexible bag 315 of package embodiment 310 will behave in general in a manner quite similar to flexible bag 15 upon opening. The principal difference will be that the unrestrained portion of the disposable diapers projecting through the opening will be somewhat more accessible than with package embodiment 10 shown in FIG. 1. The limiting factor as to how far the continuous line of weakness 360 may project into front and back panels 40 and 41, respectively, is governed by the requirement that the carrying handle 80 not be rendered ineffective in the event the user wishes to carry the bag by its handle after opening.

Figure 4:
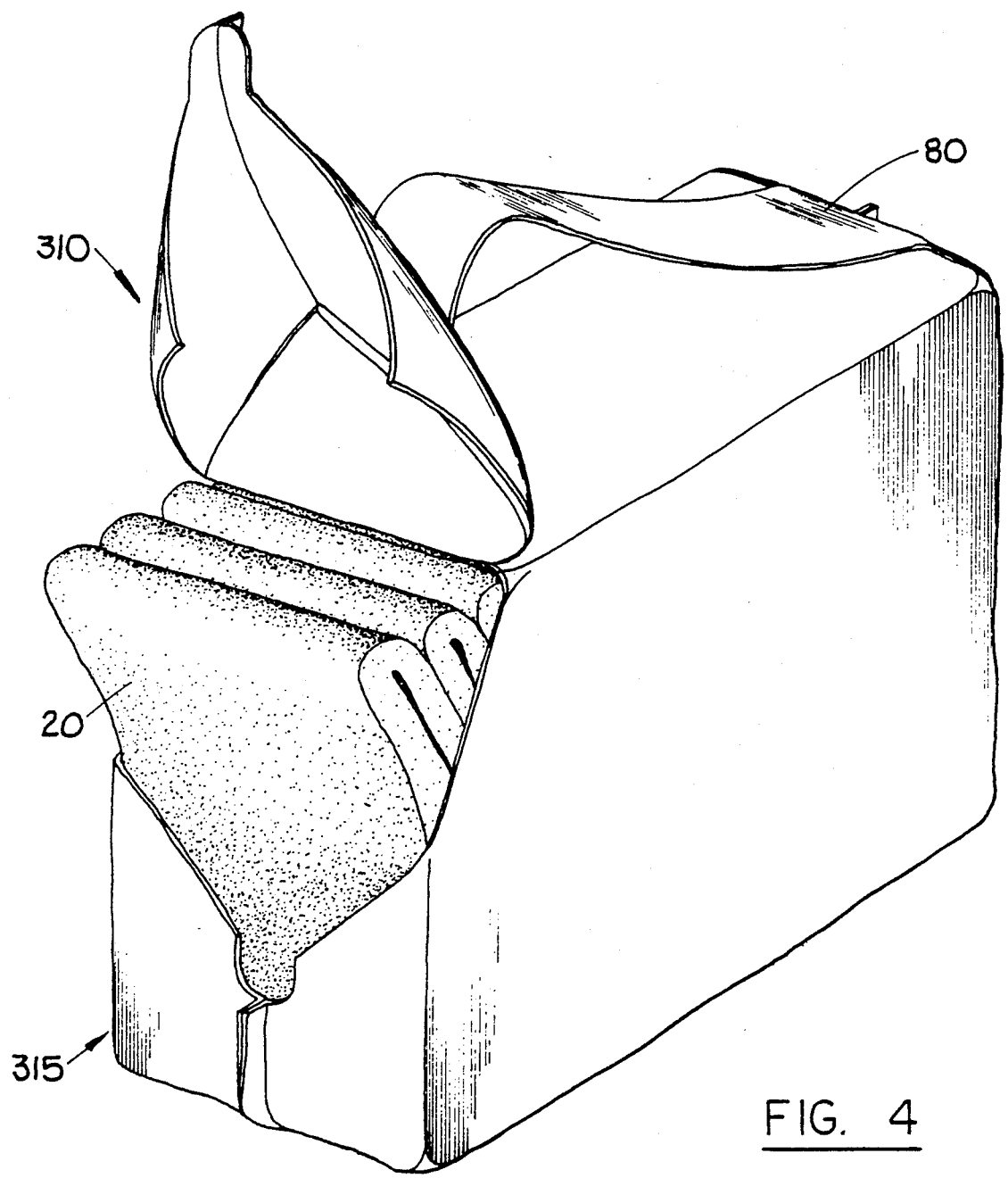
FIG. 4 is a view of the bag generally shown in FIG. 3 after the easy opening feature has been activated and the portion of the bag defined by the line of weakness partially removed from the remainder of the bag.

FIG. 4 shows the package embodiment 310 of FIG. 3 after activation of the easy open feature.

Figure 5:
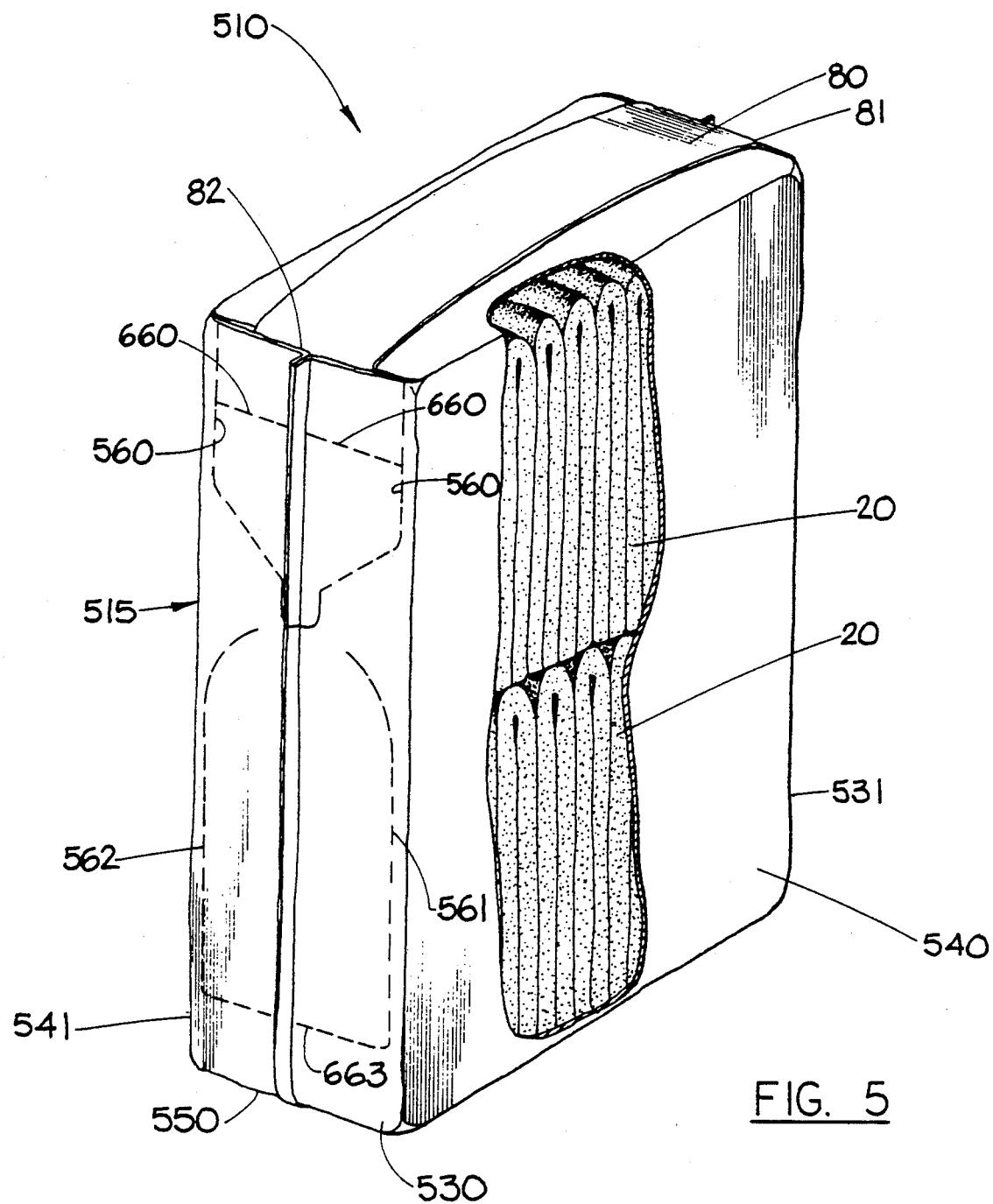
FIG. 5 is a simplified perspective view of an alternative flexible bag of compressed articles of the present invention containing two stacks of compressed flexible articles and an additional easy opening segment located on the lowermost portion of the bag's side panel.

FIG. 5 discloses an alternative embodiment 510 of an easy open flexible package containing two stacks of flexible articles maintained in a state of compression in a direction substantially parallel to their thickness. Embodiment 510 is somewhat similar to embodiment 10 shown in FIG. 1 with the exception that an additional line of weakness comprising lines of perforation 561,562 has been provided to expose the bottom section of the bag adjacent to the lowermost row of compressed diapers 20 after the top portion of the bag has been emptied.

As will also be apparent from FIG. 5, partial removal of the portion of side panel 530 defined by line of perforations 560 leaves ancillary lines of perforation 561 and 562 undisturbed. Thus, the entire lowermost stack of disposable diapers 20 is maintained under compression until the uppermost stack of diapers has been exhausted and the user intentionally ruptures lines of perforation 561, 562 to similarly expose the uppermost portion of the lowermost stack of diapers in a fan-like array.

As will be appreciated by those skilled in the art, flexible bags 515 of the present invention may, if desired, be provided with lines of perforation 660 and 663 in addition to lines of perforation 560, 561 and 562. Optional lines of perforation 660 and 663 would allow the end user to select whether to completely remove a portion of the bag's side panel 530 after opening or to leave it attached as in flexible package embodiment 10 shown in FIG. 1. It is of course recognized that ancillary line of perforations 660, if employed at all, must be so positioned on the side panel 530 of flexible bag 515 that it will not significantly weaken or otherwise impair the functionality of carrying handle 80 in its area of attachment 82 to side panel 530.

It is also recognized, that if the line or lines of weakness employed in the easy opening features of the present invention are comprised of perforations, the nature of the perforations may be altered from linear slits aligned in a parallel array along a common axis to offset, zippertooth or other types of patterns wherein precise positioning of the lines of perforation along the side panel 531 of the flexible bag 515 is less critical. For example, perforations exhibiting a degree of lateral extension may be particularly desirable in situations where the bag is finally assembled and/or erected after perforating.

While the present invention has been described in the context of an easy open flexible bag containing flexible compressed disposable diapers, it is recognized that the present invention may also be practiced to advantage in many other applications and environments. Specifically, it is recognized that the easy open feature of the present invention may be practiced on flexible bags of articles which are not subject to compression within the bag prior to opening. It will be obvious to those skilled in the art that various changes and modifications can be made without departing from the spirit and scope of the present invention, and it is intended to cover in the appended claims all such modifications that are within the scope of this invention.

What is claimed is:

1. An easy open substantially rectangular flexible bag of compressed flexible articles, said flexible articles being arranged in a stack and held in compression in a direction substantially parallel to their thickness, said bag of articles comprising:
   (a) a front and a back panel connected to one another by means of a pair of side panels, a bottom panel and a top panel, all of said panels being comprised of flexible material;
   (b) a stack of compressed flexible articles, *each of said article having a pair of opposed, substantially planar surfaces, said articles being* oriented so that [the] *said* substantially planar [surface of said articles is] *surfaces are* aligned substantially parallel to the side panels of said bag and the outermost peripheral edges of the articles contained within said stack are aligned substantially parallel to the front, back, bottom and top panels of said bag, whereby the entire exposed substantially planar surface of the outermost article at each end of said stack intimately contacts the innermost surface of the adjacent side panel, while only the outermost peripheral edges of said articles contained within said stack contact said front, back, top and bottom panels, said side panels and said front and back panels being subject to tension imposed by said stack of compressed flexible articles, said top and bottom panels being in a substantially untensioned condition; [and]
   (c) a carrying handle overlying said top panel of said bag, said carrying handle having its opposing ends secured to the opposing side panels of said bag; and
   (d) an easy open device comprising a substantially continuous line of weakness located at least partially within one of said tensioned side panels, said substantially continuous line of weakness defining a predetermined portion of said side panel to be at least partially separated from the remainder of said side panel without releasing the tension in the remainder of said side panel and without impairing the functionality of said carrying handle, said predetermined portion of said side panel having a total surface area amounting to as much as about 75 percent of the total surface area of one of said substantially planar surfaces of said articles contained in said stack, whereby said predetermined portion of said side panel is at least partially separated from the remainder of said side panel by applying a grasping force to said predetermined portion of said side panel defined by said line of weakness to propagate tears along said line of weakness, whereupon the portion of the stack of articles coinciding with the aperture thus formed in said side panel expands through said aperture in a fan-like array while the portion of said stack coinciding with the remaining tensioned portion of said side panel is retained in a substantially compressed condition.

2. The flexible bag of compressed flexible articles of claim 1, wherein a readily visible, unobstructed tear initiating point is provided in the side panel at least partially containing said line of weakness, said tear initiating point being located along said line of weakness.

3. The flexible bag of compressed flexible articles of claim 2, wherein the lowermost portion of said line of weakness in said side panel converges to form an arrow having a tip pointing generally in the direction of the bottom of said bag and wherein the tip of said arrow includes a readily accessible grasping tab comprising said tear initiating point for initiating said tears along said line of weakness.

4. The flexible bag of compressed flexible articles of claim 3, said bag further including graphical indicia to direct the user's attention to said grasping tab comprising said tear initiating point.

5. The flexible bag of compressed flexible articles of claim 4, wherein said graphical indicia on said bag are on said side panel at least partially containing said line of weakness.

6. The flexible bag of compressed flexible articles of claim 1, wherein the material comprising said flexible bag is selected from the group consisting of polymeric films, papers, nonwovens and laminate structures comprised of two or more of the aforementioned materials.

7. The flexible bag of compressed flexible articles of claim 6, wherein the material comprising said carrying handle is selected from the group consisting of polymeric films, papers, nonwovens and laminate structures comprised of two or more of the aforementioned materials.

8. The flexible bag of compressed flexible articles of claim 6, wherein said line of weakness is comprised of perforations in the material comprising said flexible bag.

9. An easy open substantially rectangular flexible bag of compressed flexible articles, said flexible articles being arranged in a stack and held in compression in a direction substantially parallel to their thickness, said bag of articles comprising:
   (a) a front and a back panel connected to one another by means of a pair of side panels, a bottom panel and a top panel, all of said panels being comprised of flexible material;
   (b) a stack of compressed flexible articles, each of said articles having a pair of opposed, substantially planar surfaces, said articles being oriented so that said substantially planar surfaces are aligned substantially parallel to the side panels of said bag and the outermost peripheral edges of the articles contained within said stack are aligned substantially parallel to the front, back, bottom and top panels of said bag, whereby the entire exposed substantially planar surface of the outermost article at each end of said stack intimately contacts the innermost surface of the adjacent side panel, while only the outermost peripheral edges of said articles contained within said stack contact said front, back, top and bottom panels, said side panels and said front and back panels being subject to tension imposed by said stack of compressed flexible articles, said top and bottom panels being in a substantially untensioned condition;

(c) a carrying handle overlying said top panel of said bag, said carrying handle having its opposing ends secured to the opposing side panels of said bag; and (d) an easy open device comprising a substantially continuous line of weakness located partially within one of said tensioned side panels and extending into the uppermost corners of the adjacent front and back panels of said bag, said substantially continuous line of weakness defining a predetermined portion of said side panel to be at least partially separated from the remainder of said side panel without releasing the tension in the remainder of said side panel and without impairing the functionality of said carrying handle, said predetermined portion of said side panel having a total surface area amounting to as much as about 75 percent of the total surface area of one of said substantially planar surfaces of said articles contained in said stack, whereby said predetermined portion of said side panel is at least partially separated from the remainder of said side panel by applying a grasping force to said predetermined portion of said side panel defined by said line of weakness to propagate tears along said line of weakness, whereupon the portion of the stack of articles coinciding with the aperture thus formed in said side panel expands through said aperture in a fan-like array while the portion of said stack coinciding with the remaining tensioned portion of said side panel is retained in a substantially compressed condition.

10. The flexible bag of compressed flexible articles of claim 9, wherein a readily visible, unobstructed tear initiating point is provided in the side panel at least partially containing said line of weakness, said tear initiating point being located along said line of weakness.

11. The flexible bag of compressed flexible articles of claim 10, wherein the lowermost portion of said line of weakness in said side panel converges to form an arrow having a tip pointing generally in the direction of the bottom of said bag and wherein the tip of said arrow includes a readily accessible grasping tab comprising said tear initiating point for initiating said tear along said line of weakness.

12. The flexible bag of compressed flexible articles of claim 11, said bag further including graphical indicia to direct the user's attention to said grasping tab comprising said tear initiating point.

13. The flexible bag of compressed flexible articles of claim 12, wherein said graphical indicia on said bag are on said side panel at least partially containing said line of weakness.

14. The flexible bag of compressed flexible articles of claim 9, wherein the material comprising said flexible bag is selected from the group consisting of polymeric films, papers, nonwovens and laminate structures comprised of two or more of the aforementioned materials.

15. The flexible bag of compressed flexible articles of claim 14, wherein the material comprising said carrying handle is selected from the group consisting of polymeric films, papers, nonwovens and laminate structures comprised of two or more of the aforementioned materials.

16. The flexible bag of compressed flexible articles of claim 14, wherein said line of weakness is comprised of perforations in the material comprising said flexible bag.

* * * * *

UNITED STATES PATENT AND TRADEMARK OFFICE
CERTIFICATE OF CORRECTION

PATENT NO. : 5,054,619
DATED : Oct. 8, 1991
INVENTOR(S) : Delmar R. Muckenfuhs

It is certified that error appears in the above-identified patent and that said Letters Patent is hereby corrected as shown below:

Title Page:

In the REFERENCES CITED Section, "2,506,459" should read -- 2,506,021 --

In the ABSTRACT, line 12, "includesa" should read -- includes a -- .

In the REFERENCES CITED Section, page 2, "Mackenfuhs" should read -- Muckenfuhs -- .

Column 3, line 68, after "75%" insert -- of the cross-sectional shape -- .

Column 8, line 46, "VI" should read -- $V_1$ -- .

Column 9, line 4, after "50%" delete the period -- . -- and insert therefor a comma -- , -- .

Column 11, line 29, delete " [the] " .

Column 11, line 30, delete "[surface of said articles is] ".

Column 11, line 46, delete "[and]".

Signed and Sealed this

Thirteenth Day of April, 1993

Attest:

STEPHEN G. KUNIN

Attesting Officer

Acting Commissioner of Patents and Trademarks